United States Patent [19]
Rizik

[11] Patent Number: 5,628,761
[45] Date of Patent: May 13, 1997

[54] GUIDE WIRE PASSAGE CREATION DEVICE

[76] Inventor: David G. Rizik, 10480 E. Larkspur Dr., Scottsdale, Ariz. 85259

[21] Appl. No.: 495,366

[22] Filed: Jun. 28, 1995

Related U.S. Application Data

[63] Continuation-in-part of Ser. No. 272,889, Jul. 8, 1994, abandoned.

[51] Int. Cl.$^6$ .................................................... A61B 17/32
[52] U.S. Cl. ........................ 606/170; 606/159; 604/101
[58] Field of Search ................................. 606/159, 170, 606/171; 604/101, 96

[56] References Cited

U.S. PATENT DOCUMENTS

| | | | |
|---|---|---|---|
| 4,445,509 | 5/1984 | Auth | 604/266 |
| 4,589,412 | 5/1986 | Kensey | 128/305 |
| 4,781,186 | 11/1988 | Simpson et al. | 128/305 |
| 4,784,636 | 11/1988 | Rydell | 604/22 |
| 4,790,813 | 12/1988 | Kensey | 604/22 |
| 4,846,174 | 7/1989 | Willard et al. | 128/344 |
| 4,895,560 | 1/1990 | Papantonakos | 604/22 |
| 4,898,575 | 2/1990 | Fischell et al. | 604/22 |
| 4,923,462 | 5/1990 | Stevens | 606/159 |
| 4,926,858 | 5/1990 | Gifford, III et al. | 606/159 |
| 4,983,165 | 1/1991 | Loiterman | 604/101 |
| 4,993,412 | 2/1991 | Murphy-Chutorian | 606/7 |
| 5,026,366 | 6/1991 | Leckrone | 606/7 |
| 5,026,384 | 6/1991 | Farr et al. | 606/159 |
| 5,047,040 | 9/1991 | Simpson et al. | 606/159 |
| 5,100,424 | 3/1992 | Jang et al. | 606/159 |
| 5,179,961 | 1/1993 | Littleford et al. | 604/101 |
| 5,188,632 | 2/1993 | Goldenberg | 606/7 |
| 5,222,966 | 6/1993 | Perkins et al. | 606/159 |
| 5,290,275 | 3/1994 | Kittrell et al. | 606/15 |
| 5,292,315 | 3/1994 | Euteneuer | 604/280 |
| 5,303,714 | 4/1994 | Abele et al. | 128/772 |
| 5,320,634 | 6/1994 | Vigil et al. | 606/159 |
| 5,334,207 | 8/1994 | Gay, Jr. | 606/7 |
| 5,342,292 | 8/1994 | Nita et al. | 604/22 |
| 5,350,375 | 9/1994 | Deckelbaum et al. | 606/7 |
| 5,395,311 | 3/1995 | Andrews | 604/22 |
| 5,409,453 | 4/1995 | Lundquist et al. | 604/22 |
| 5,474,530 | 12/1995 | Passafaro et al. | 604/22 |
| 5,476,450 | 12/1995 | Ruggio | 606/159 X |

OTHER PUBLICATIONS

M. Freed, C. Grines, eds., *Manual of Interventional Cardiology*, Chapter 11, Section E.3, pp. 155–156.

*Primary Examiner*—Michael Powell Buiz
*Assistant Examiner*—Patrick W. Rasche
*Attorney, Agent, or Firm*—Gifford, Krass, Groh, Sprinkle, Patmore, Anderson & Citkowski, P.C.

[57] ABSTRACT

A device to be used in connection with revascularization, especially of the coronary arteries, makes it possible for conventional techniques such as angioplasty or atherectomy to be employed in totally or severely occluded blood vessels deemed otherwise impassable by a guide wire. A guide wire passage is created by providing a catheter with a retractable cutting head or laser source that penetrates the atheromatic material in a blood vessel. The device is centered and stabilized in the vessel by a circumferential balloon so that the passage through the atheromatic material is in the desired direction. The circumferential balloon also prevents blood flow in the event of a break in the blood vessel wall.

6 Claims, 3 Drawing Sheets

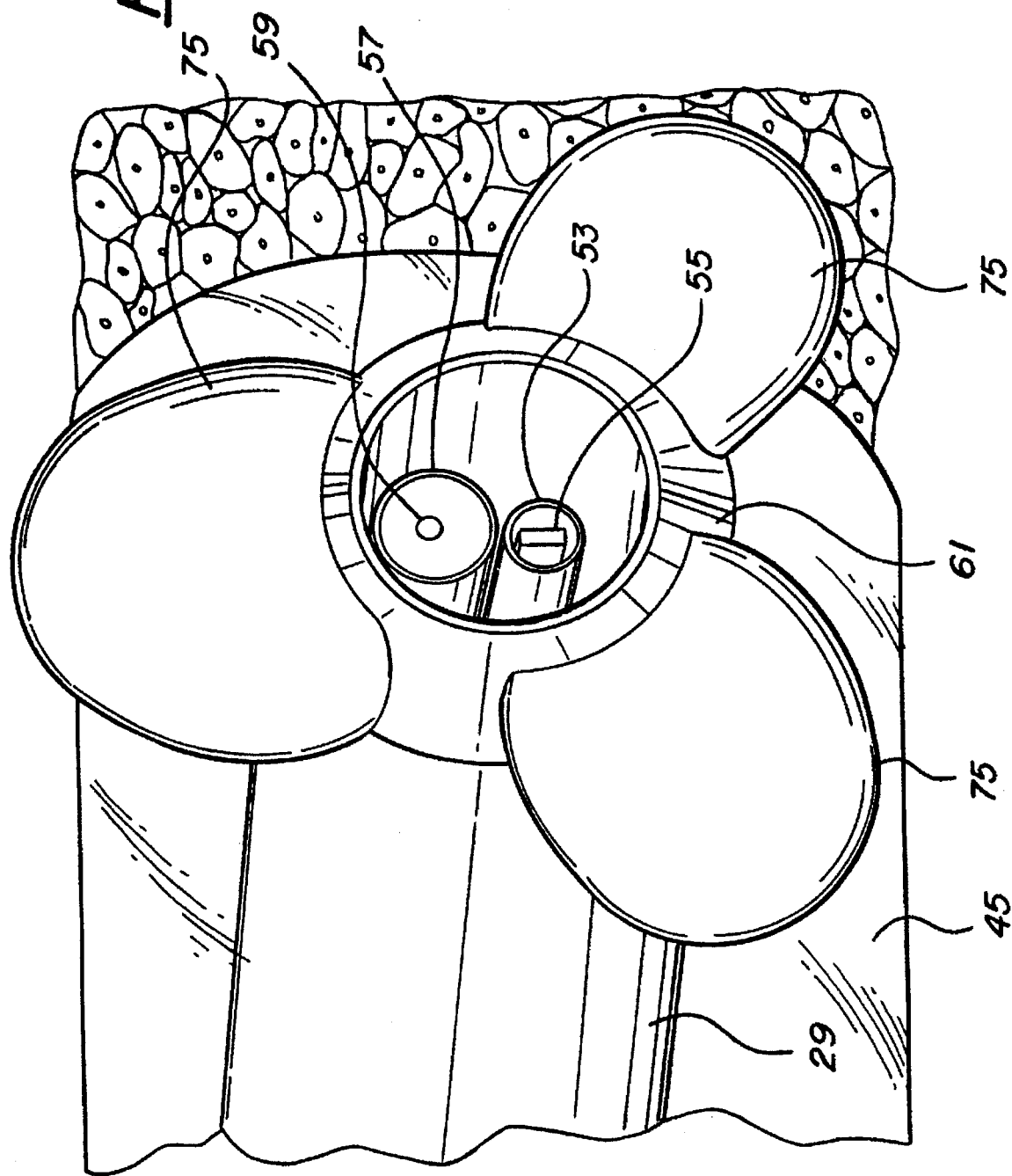

GUIDE WIRE PASSAGE CREATION DEVICE

REFERENCE TO RELATED APPLICATIONS

This application is a continuation-in-part of Ser. No. 08/272,889, filed Jul. 8, 1994 now abandoned.

FIELD OF THE INVENTION

This invention is a device to be used in connection with revascularization, especially of the coronary arteries. In particular, the present invention makes possible the employment of conventional techniques such as angioplasty or atherectomy in totally or severely occluded blood vessels deemed impassable by a guide wire because it creates a guide wire passage in such blood vessels easily and quickly.

BACKGROUND OF THE INVENTION

In percutaneous revascularization a blood vessel whose interior is occluded by atheromatic material (also called plaque) is treated so that the flow of blood through the artery is increased. The treatment is performed under anesthesia with a fluoroscope to allow the physician to view the procedure. In the case of occluded coronary arteries, the revascularizing device is inserted in the groin area and threaded through the patient's circulatory system to the heart.

In the current state of the art, revascularization is accomplished by balloon angioplasty, laser angioplasty and rotational and directional atherectomy. All these techniques require that as a first step a guide wire be passed through the occlusion. Whether that first step can be accomplished, however is often a function of: (1) the duration (age) of the occlusion; (2) the pathophysiologic mechanism by which the occlusion occurs; and (3) the length of the occlusion. This requirement, to be able to pass a guide wire through a coronary artery occlusion, has been one of the Achilles heels of interventional cardiology. In arteries that are deemed impassable by a guide wire, the cardiologist has had no choice but to perform bypass surgery. This has been the case for patients known to have total or severe occlusions as well as for those whose occlusions are only discovered to be impassable by a guide wire after a revascularization procedure has begun, such as because there is calcification that does not appear on angiography. There are also situations involving arteries that are unusually tortuous or have unusually fragile walls. Bypass surgery, however, is more costly, invasive and complicated than revascularization. Bypass surgery also involves lengthier operating room scheduling, slower recovery time, and higher incidence of increased morbidity and mortality. There is therefore a need for a device that can prepare an impassably occluded artery for revascularization by creating a passage for a guide wire.

There is also a need for a device of this type that is simple to manufacture and simple and quick to use. Such a device should be easy to insert up to an occlusion in a blood vessel, should easily and reliably create a passage for a guide wire through the occlusion in that vessel, and should be easy to withdraw so that a revascularization procedure can be performed.

Guide wires and catheters used for revascularization must travel a long distance in the circulatory system. The physician's control of those devices is remote from the leading or distal end because the control must be accomplished outside the body at the proximal end. Then, too, the arteries of some patients are quite tortuous and the atheromatic material of some patients is quite hard. Because of one or more of such factors, rupture of the artery wall at or near the site of an occlusion may occur. Consequently, there is a need for a simple guide wire passage creation device that includes features to: prevent blood flow should a rupture occur, avoid transmission of unnecessary pressure against the artery wall, and permit physician control over both the direction and the extent of travel of the passage-creating means.

Prior Art Revascularization Catheters

Prior art atherectomy catheters can only be used for stenoses a guide wire can pass through. They are either "over-the-wire" devices or carry an attached guide wire. In addition, such catheters must be capable of cutting through and removing large amounts of atheromatic material. This means that the cutter must be fairly large and strong and that the catheter must include a way to remove the excess debris of atheromatic material to prevent its introduction into the patient's bloodstream. As a consequence, such catheters are complicated and carry complex apparatus at the distal end, rendering them unsuitable for quick and easy insertion and removal in a coronary artery to create a passage for a guide wire.

Designers as well as users of atherectomy catheters have been concerned with the diameter and length of the cutting head: they want the diameter to be expandable so that the catheter is maneuverable but can cut through wide plaques and they want the length to be long enough and sturdy enough for long stenoses but short and flexible so as not to get caught in tortuous arteries. These concerns have led to ever more complex and encumbered devices, unsuitable for the simple act of guide wire passage creation or for quick and easy insertion and removal in a coronary artery.

The cutting heads of existing atherectomy catheters are typically between 2.5 and 4.0 mm in diameter. By contrast, coronary guide wires are typically less than 1 mm in diameter. A commonly used wire is 0.014 inches (0.36 mm) in diameter; the largest in current use is 0.035 inches (0.88 mm). Thus existing atherectomy catheters are unsuitable for the task of creating a passage for a guide wire without simultaneously generating atheromatic debris. Likewise, existing atherectomy catheters have cutting assemblies 5 to 10 mm. This length detracts from their ability to navigate tortuous arteries or to be inserted and removed quickly and easily.

Angioplasty catheters now available lack any means to create a passage for a guide wire. Like atherectomy catheters, they are either "over-the-wire" devices or carry an attached guide wire at the distal end. The balloons on angioplasty catheters must withstand and transmit the high pressures needed to compress plaque. Thus such balloons may be unsuitable for blocking blood flow in the event of a break in an artery wall without further trauma to the artery. Nor are they designed for centering and stabilizing the distal end of a catheter for creation of a guide wire passage. Furthermore, the specifications for angioplasty balloons are likely to be such that the balloons are costly and difficult of manufacture.

Several devices, including the atherectomy catheters made by Devices for Vascular Intervention (see, for example, U.S. Pat. No. 4,781,186 to Simpson et al), use a balloon on the distal portion of the catheter to stabilize the device within the coronary artery. However, these balloons are not circumferential around the entire distal tip of the catheter. Instead, they are located along one side of the device. Thus they are incapable of centering the distal end of the device or of preventing blood flow in the event of a break in the artery wall.

Gifford et al in U.S. Pat. No. 4,926,858 discloses an atherectomy device for severe occlusions which includes its own guide wire and an expandable member for anchoring the device. In the operation of Gifford et al's device, however, the expandable member and the guide wire must be inserted through and past the occlusion. Thus, Gifford et al require that the occlusion be traversable by both a guide wire and the collapsed expandable member. Furthermore, the expandable member is located distal to the cutting device so that debris from the cutter can be capped. Thus, unlike a balloon that is proximal to the cutting head prior to use, the expandable member of Gifford et al can not serve to center and stabilize the cutting head before and during the making of a passage for a guide wire.

In U.S. Pat. No. 4,898,575, Fischell et al provides a guide wire following tunneling catheter. This catheter can only be used on stenoses that can be traversed first by a guide wire. Thereafter the Fischell et al catheter can cut through the plaque to provide a clean hole for treatment of the stenosis with other catheters. Fischell et al assume that a guide wire can be placed through the stenosis and do not address the problem of stenoses where the guide wire cannot be pushed through.

In U.S. Pat. No. 4,589,412 to Kensey, a proximally located balloon is provided on an atherectomy device to prevent blood loss in the event of any complication in which it becomes necessary to stop the blood flow through the artery. The balloon is not otherwise inflated and thus is not for centering and stabilizing the device to facilitate control over the path and direction of the rotating cutter. Kensey's figures indicate the presence of a central passage even at the distal-most extremity of the catheter, thus implying that his device is used over a guide wire. Although there is no mention of a guide wire, Kensey's design is claimed to alleviate the need for a guiding catheter. Kensey's device is quite bulky and elaborate and is not meant to solve the problem of creating a central passageway for a guide wire in a totally or severely occluded artery to enable the use of other conventional catheters to treat the stenosis. Kensey's device also uses fluid to transmit rotational force to his atherectomy cutter, rather than mechanical means, thus making speed of insertion, use and removal more problematic.

U.S. Pat. No. 5,292,315 to Euteneuer discloses a low profile catheter used with its own guide wire. The catheter includes means to transmit axial torque to the guide wire to position a lumen size increasing means such as a balloon or ablation element to increase the opening in a partly occluded blood vessel. This does not solve the problem of possible injury to the artery wall when an attempt is made to push through atheromatic material. Nor does this catheter have means to make sure that the guide wire is pushed along the center of the artery. The torquability is apparently desired not to create a passage in a total or severe occlusion but to properly orient the pre-bent shape of the guide wire in the artery. Last, a guide wire should have certain characteristics (flexibility, thinness) that may be sacrificed in a torquable wire.

Another atherectomy device, the "Rotoblator" made by Heart Technology Incorporated, needs a wire to negotiate the occlusion before atherectomy can be performed. The rotoblator rotating burr has a cutting head which is larger in diameter than the body of its burr. It also has a hollow tip because it relies on wire guidance through the vessel. These features make it unsuitable as a guide wire passage creation device that does not leave atheromatic debris and is simple to manufacture and quick and easy to insert, use and remove.

Laser angioplasty devices such as U.S. Pat. No. 4,993,412 to Murphy-Chutorian require the device to be positioned using a guide wire that is moved through and beyond the occlusion. U.S. Pat. No. 5,334,207 to Gay, which provides a laser angioplasty device with magnetic control, is said to be usable in blood vessels which are so occluded that catheters depending on guide wires are ineffectual. Gay's device, however, employs magnetic steering and aiming of the laser tip to perform angioplasty. Although Gay employs a balloon to stabilize the laser probe tip, his balloon is located one inch from the tip and therefore cannot center the tip in the artery. For this purpose, Gay relies instead on magnetic control of the laser tip. The Gay device, which employs sufficient laser energy to fully vaporize the entire occlusion, is unsuited to the purpose of simply creating a passage for a guide wire in a tortuous occluded artery.

There is therefore a need for a small diameter simple device that is easy to make and easy and quick to insert, use and remove, that can be centered and stabilized proximal to an otherwise impassable occlusion, and that can create a passage for a guide wire in the occlusion without creating excess atheromatic debris so that the physician can take advantage of revascularization techniques dependent on prior passage of the occlusion by a guide wire.

SUMMARY OF THE INVENTION

The present invention is a device for use in a blood vessel deemed impassably occluded by atheromatic material to prepare the vessel to undergo a revascularization process in which traversal of the occlusion by a guide wire is required. The preferred embodiment is a catheter for use in the coronary arteries.

The device comprises a catheter having means for creating a passage through the atheromatic material for subsequent guide wire insertion. This guide wire passage creation means creates a passage whose diameter is no larger than necessary to permit subsequent traversal of the occlusion by a guide wire. The catheter is rigid at the distal end, for a distance of ten to twenty millimeters up to the tip. The device has at least two other lumens, in addition to the one through which the guide wire passage creation means can be deployed. The diameter of one of the other lumens allows the catheter to be inserted over a guide wire and allows the guide wire (typically 0.014 inch diameter) to be withdrawn into the catheter once the distal end of the catheter has been advanced to the atheromatic material in the occluded blood vessel. This lumen may also be used for injection of a contrast dye.

The other lumen communicates with a multipurpose means disposed circumferentially on the catheter to center and stabilize the distal end of the device when the device is positioned proximal to the atheromatic material in the occluded blood vessel. This multipurpose means also will prevent blood flow in the event of a break in the blood vessel wall.

In a preferred embodiment, this multipurpose means is an inflatable annular balloon, the guide wire passage creation device is a rotating burr or a laser (fiber bundle) no wider than 1 to 1.5 mm, the distal tip of the catheter also carries a nose cone, there is a set of smaller balloons disposed at approximately equal angular positions around the distal end of the annular balloon, proximally adjacent the nose cone, which can be selectively inflated to refine the position of the nose cone and to make intimate contact with the artery wall, and the guide wire passage creation means can be advanced beyond the distal tip of the catheter a short distance, and is retractable back into the catheter.

The invention also includes the method of using such a device for creating a guide wire passage in atheromatic material in totally or severely occluded blood vessels. In the method, a guide wire is placed in the artery up to the occlusion, the catheter is placed over the guide wire and advanced in the blood vessel until it abuts the occlusion. A means to center and stabilize the distal end of the device is deployed and then the guide wire passage creation means is deployed to create a passage for a guide wire through the atheromatic material.

BRIEF DESCRIPTION OF THE DRAWINGS

FIG. 3 is a view of another embodiment of the catheter showing the annular balloon, the smaller distal balloons and the nose cone.

DETAILED DESCRIPTION OF THE INVENTION

Figure 1:
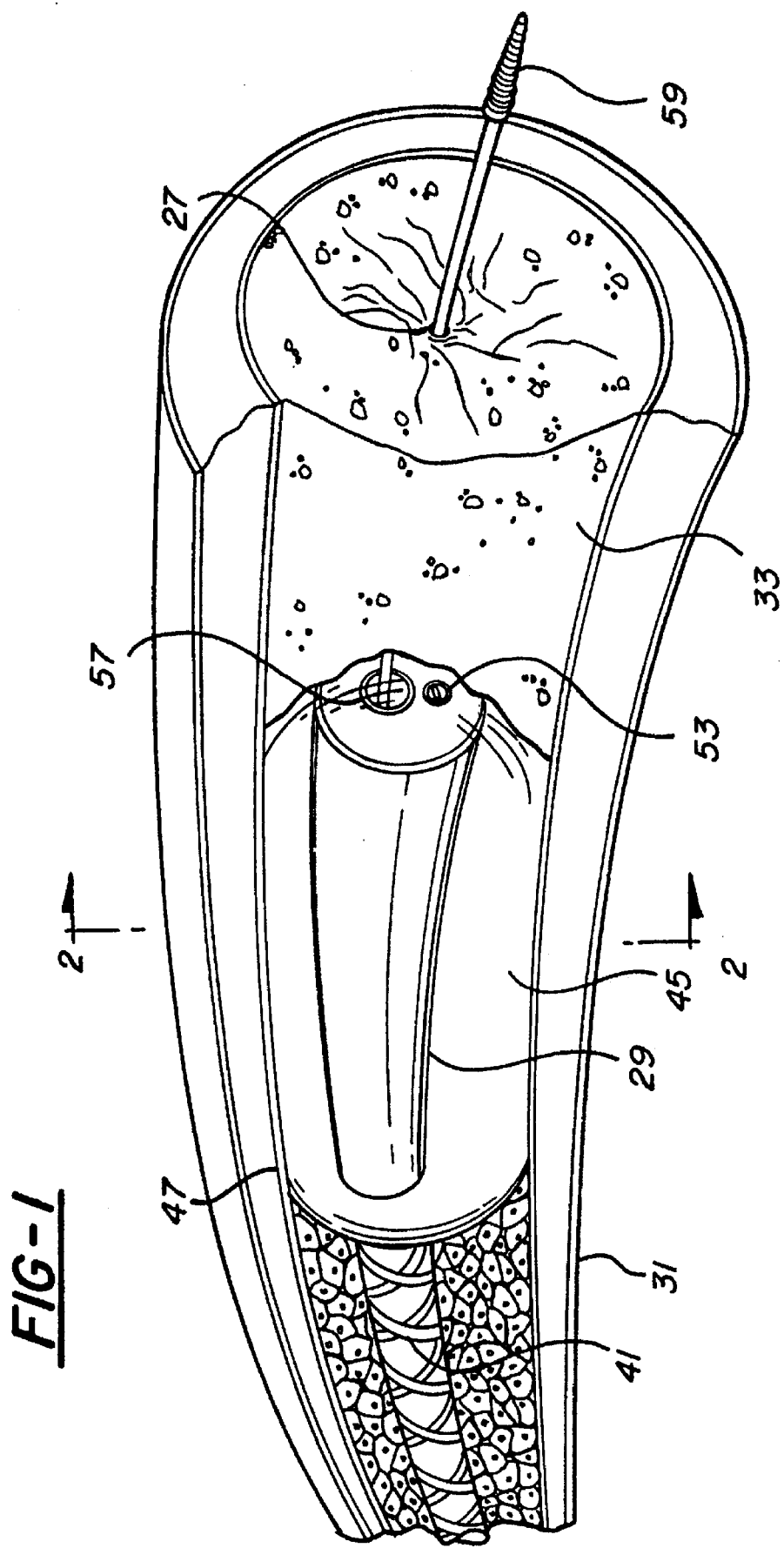
FIG. 1 is a cut-away view of the distal end of one embodiment of the device where it has been advanced in an occluded artery to abut an occlusion and the rotating burr has been advanced through the occlusion to create a passage for a guide wire.

The concept of using a guide wire passage creation device is unique in both the technique by which it is used and its configuration relative to other coronary artery devices. The device is described below in connection with its use in a coronary artery although it can be used in other occluded blood vessels.

A guiding catheter is placed into a coronary artery. A guide wire is placed through the guiding catheter and advanced up to the point of the total or nearly total occlusion in the coronary artery. The guide wire passage creation device is then placed through the guiding catheter over the guide wire and also advanced to the occlusion such that the distal most end (a nose cone, for example) abuts the total occlusion. The guide wire is then pulled back into the device so that only the leading edge of the catheter is placed up against the occlusion.

A guide wire passage creation means can then be deployed to create a centered passage in the occlusion so that a guide wire can subsequently traverse the occlusion. This passage creation means creates a passage, such as by cutting, boring, drilling, vaporizing or dissolving, that is suitable, but no larger than necessary, for a guide wire. The limitation on diameter of the passage minimizes the risk of a) unnecessarily dislodging atheromatic material and b) perforation of the artery wall.

The diameter of most (unoccluded) coronary arteries is, on average, about 3.5 mm, the largest arteries being 4 or even 5 mm. Atherectomy and angioplasty devices have been designed to remove or compress plaque essentially all the way to the artery wall. Thus, the cutting head or angioplasty balloon (fully inflated) of such devices typically have diameters of 2 or 3 mm or even larger. By contrast, the guide wire passage creation device at its widest at the distal end (before deployment of the circumferential balloon described below to center and stabilize the device in the artery) is preferably less than 2 mm.

A number of features make it possible to center and stabilize the guide wire passage creation means so that the passage is well-centered in the artery. This further minimizes the risk of injury to the artery wall by misdirection of the passage creation means. One such feature is that the distal end of the catheter is somewhat rigid for a short distance on the order of ten to twenty millimeters. A metal alloy can be used to provide the rigidity. This rigidity in effect straightens out the artery immediately proximal to the occlusion so that the direction in which the cutting means travels is better centered in the occluded portion of the artery. With this goal in mind, the length of the rigid portion is necessarily limited to less than about one inch. Another feature is a circumferential balloon at the distal end of the catheter. The balloon when inflated will make intimate contact with the artery wall at one or more points. The balloon is preferably coaxial with, and about the same length as, the rigid portion of the catheter, so that the balloon and the rigid portion cooperate in the centering and stabilizing of the guide wire passage creation means in the artery.

In case of a rupture in the artery wall, the inflated balloon can be positioned to prevent blood flowing out of or down the perforated artery to serve as a safety mechanism until bypass surgery can be performed. Currently, some interventionalists will place an angioplasty balloon in a coronary artery which has been perforated. The original intention of the angioplasty balloon was not to serve in this function. The balloon on the present device serves a primary role as an occluding device should a perforation occur. The inflated diameter of the balloon can be 2.5 mm, 3.0 mm, 3.5 mm and 4.0 mm.

Because of the rigidity of the distal end of the device and the long balloon, the passage creation means may be advanced distally without guidance via a guide wire. The extent of advancement may be limited to about ten to twenty millimeters by a conventional stop mechanism at the proximal end of the catheter.

Once the balloon structure is inflated to stabilize the catheter within the artery, the guide wire passage creation means is advanced into the "meat" of the occlusion. By slow and deliberate advancement, a passage is made into the total occlusion. Confirmation of this passage may be accomplished by injecting contrast agent into the proximal portion of the catheter through the guide wire lumen. The guide wire passage creation means can then be withdrawn and attempts to pass the guide wire can be made. Once the guide wire negotiates the newly formed passage in the coronary artery, the device can then be removed in similar fashion as the current standards for exchanging balloons or atherectomy catheters. Thus the guide wire remains in the distal aspect of the coronary artery through the passage made by the present invention. The doctor may then choose a conventional revascularization technique (such as balloon angioplasty, laser angioplasty or atherectomy) to treat the occlusion.

In one embodiment, the guide wire passage creation means is a rotating burr which is advancable axially to about ten to twenty millimeters beyond the distal tip of the catheters. This extent of motion balances the need for creation of a passage in a long occlusion, on the one hand, with avoidance of perforation of the artery wall by off-center advancement of the cutting means, on the other. In a preferred embodiment of the rotating burr, the tip of the burr is blunt (olive-shaped) rather than pointed.

In a variant of the rotating burr embodiment, a suction bottle apparatus may be provided at the proximal end of the device, and the rotating burr is attached to a shaft that runs from the suction bottle. The shaft, as well as the burr itself, are hollow to permit suctioning of any material dislodged during rotational movement. This feature will assist in preventing distal embolization of material in the arterial tree. If, during the procedure, poor flow or the absence of any "reflow phenomenon" suggest to the cardiologist that distal embolization may have occurred, pharmacological agents may be injected through this shaft, the rotating burr and out through the nose cone. In embodiments where the guide wire passage creation means is not a hollow rotating burr, the guide wire lumen may be used for injection of such agents.

In an alternative embodiment, the guide wire passage creation means may employ laser energy or ultrasound, and can be immovable with respect to the distal end of the device. For example, when the laser is first fired, it will create a short passage for a guide wire in the atheromatic material. Then, in a winding blood vessel, the entire device may be advanced (perhaps slightly deflating the balloon) to proceed through the rest of the occlusion. In a straighter blood vessel, or one with a shorter occlusion, continued firings of the laser will lengthen the guide wire passage without having to advance the cutting head or entire device at all. For more tortuous arteries where the severe or total occlusions are longer in extent, a device in which the laser cutting means is axially movable may be employed.

In another embodiment, the guide wire passage creation means may be a syringe through which the cardiologist can administer a chemical agent that can dissolve the atheromatic material in the vicinity of the syringe tip. Because only a guide wire passage is desired to be created, rather than complete destruction or removal of the atheromatic material, the chemical agent can be used in minute amounts and damage to the artery wall kept to a minimum. The centering and stabilizing provided by the balloon also serve to control and limit the tissue with which the chemical agent may come in contact.

In order to refine more precisely the position of the distal tip of the catheter prior to deploying the guide wire passage creation means, a cluster of small balloons is provided in one embodiment of the device. These balloons, attached to the distal end of the annular balloon immediately proximal of the nose, or to the nose cone itself, are positioned at approximately equal angular positions around the device and approximately the same longitudinal position. Depending on the number of balloons they can be slightly staggered longitudinally and bunched radially, although preferably there are three balloons at the same longitudinal position and at equal angular positions. These smaller refinement balloons (which may be referred to as the "tri-balloon structure") may be individually or simultaneously inflated to steer the nose cone in the desired direction. This would allow better centering of the device in the artery to reduce the risk of arterial when deploying the guide wire passage creation means.

Now with reference to the figures, there is shown a guide wire passage creation device which includes a catheter having a rigid section and balloon at its distal end. In FIG. 1, catheter 41 is advanced in artery 31 over a guide wire which is in lumen 53. There is atheromatic material 33 totally or severely occluding artery 31 such than the guide wire can penetrate the center of the artery not at all or only with great difficulty. The exterior of the distal end of the main catheter lumen 47 has a rigid portion 29 and a circumferential balloon 45 which secures and stabilizes the distal end of the catheter once the occlusion has been reached. Rotating burr 59, which is in lumen 57, is shown advanced through occlusion 33, having been deployed to create passage 27 for a guide wire.

Figure 2:
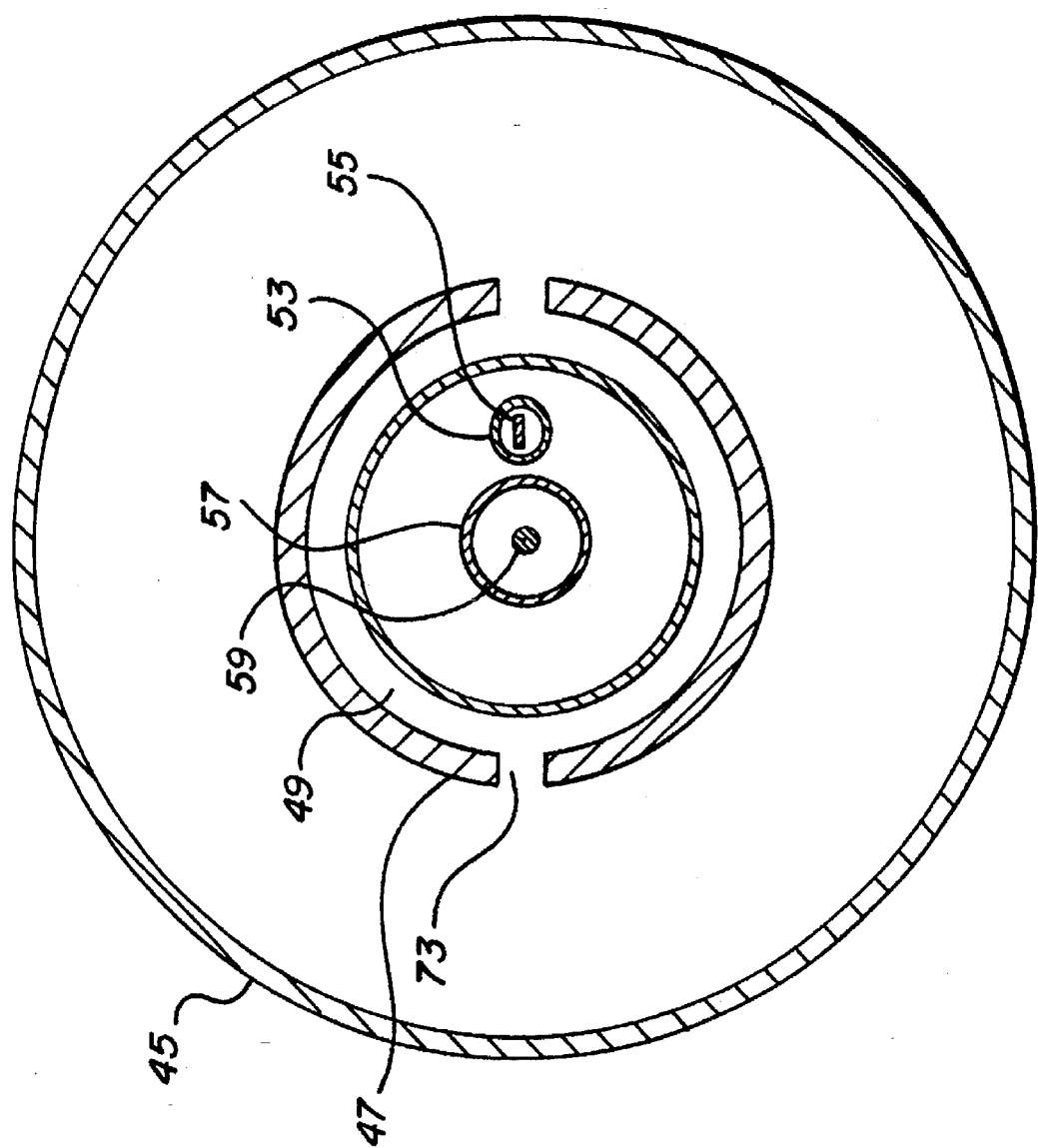
FIG. 2 is a cross-sectional view of the distal end of one embodiment of the catheter taken through 2—2 of FIG. 1.

Proceeding to FIG. 2, there is shown a cross-section inside the main exterior lumen 47 at line 2—2 of FIG. 1. Annular balloon 45 is shown in its inflated position. (It should be understood that when the catheter is first introduced in the artery, annular balloon 45 is not inflated but lies against main exterior lumen wall 47.) Fluid for inflating balloon 45 may be introduced through annular passage 49. Inside main lumen 47 are two adjacent lumens 53 and 57. Lumen 53 is provided for the passage of guide wire 55 and lumen 57 is provided for the guide wire passage creation means 59. The motion of the guide wire passage creation means 59 is controlled at the proximal end of the device (not shown) by hand operated means including a stop mechanism which limits the travel of the rotating burr to no more than ten to twenty millimeters beyond the distal end of the catheter. Port 73 opens into annular passage 49 for the purpose of allowing balloon 45 to be inflated. Guide wire passage creation means 59 may be a laser fiber bundle or a drill bit, or a pointed rod coated with a hard abrasive substance such as diamond which can cut through the occluded material when the rod is rotated. Other forms of guide wire passage creation means are also possible.

In the rotating burr embodiment, the rotating burr may be a millimeter or two long or up to one or two centimeters. Catheters of the present invention may come in different sizes of burr diameters and/or burr lengths or the retractable head may be a separate piece (available in a variety of sizes) that is selected and attached to the rest of the catheter by the cardiologist as appropriate.

Nose cone 61 is shown in FIG. 3. The purpose of the nose cone is to stabilize the distal end of the catheter while the physician deploys the guide wire passage creation means in the atheromatic material.

FIG. 3 also shows the configuration of balloons used to refine the positioning of the guide wire passage creation means prior to and during its development. In a preferred embodiment, two or more (preferably three) balloons 75 are arranged around the distal end of annular balloon 45 on nose cone 61 at substantially equal angular positions and are selectively inflatable and deflatable via additional lumens in the catheter (not shown) to enable the physician to precisely position the distal end of the catheter, in particular nose cone 61. The tri-balloon refinement structure 75, when deployed, makes intimate contact with the interior of the artery wall. The location of the physical attachment of the tri-balloon structure 75 may be at the distal end of annular balloon 45, although refinement balloons 75 when inflated may extend to at least partially encircle nose cone 61.

At the proximal end of the catheter a motorized unit (not shown) may be employed to advance the guide wire passage creation means into the occlusion once the catheter is properly positioned. The motorized unit or manual control may limit the travel distance of the guide wire passage creation means.

Although this invention for creating a guide wire passage in a totally or severely occluded coronary artery is described in connection with the preferred embodiment, it will be evident to those skilled in the art that the device and method has application in other embodiments and other blood vessels.

What I claim is:

1. A guide wire passage creation device for use in a blood vessel impassably occluded by atheromatic material, the device being adapted to enable a subsequent revascularization process requiring traversal of the occlusion by a guide wire, the device comprising:

a catheter having proximal and distal ends, the distal end culminating in a tip;

means for creating a passage through the atheromatic material for subsequent guide wire traversal, the guide wire passage creation means being adapted to create a passage whose diameter is no larger than necessary to permit subsequent traversal by a guide wire;

the catheter having at least three lumens, comprising:

a first lumen having a diameter no greater than about 0.02 inches, for insertion of a guide wire and for injection of a contrast dye, a second lumen including the guide wire passage creation means, and a third lumen communicating with an annular balloon disposed circumferentially at the distal end of the catheter adjacent the tip, the annular balloon having proximal and distal ends, and further comprising a plurality of smaller balloons disposed around the distal end of the annular balloon and spaced at approximately equal angular positions around the circumference of the annular balloon, the smaller balloons being selectively inflatable and deflatable to make intimate contact with the wall of the blood vessel to refine the position of the guide wire passage creation means in the vessel the annular balloon performing the following functions:

centering the distal end of the device when the distal tip of the device is positioned immediately proximal to the atheromatic material in the occluded blood vessel, stabilizing the distal end of the device when the distal tip of the device is positioned immediately proximal to the atheromatic material in the occluded blood vessel, and preventing blood flow in the event of a rupture in the blood vessel wall; and operator controlled means at the proximal end of the device for deploying the multipurpose means and for deploying the guide wire passage creation means;

wherein the distal end of the catheter is substantially rigid from the tip to a distance beginning no less than about 10 millimeters and no more than about 20 millimeters from the tip, and wherein the multipurpose means is coaxial with the rigid portion of the catheter, so that the rigid portion and multipurpose means cooperatively act to center and stabilize the guide wire passage creation means in the blood vessel.

2. The device of claim 1, wherein the guide wire passage creation means is movable axially with respect to the catheter from a first position, at which the guide wire passage creation means is substantially within the multipurpose circumferential means, to a second position, up to about 20 millimeters in a distal direction beyond the distal tip of the catheter.

3. The device of claim 2 further comprising a hollow nose cone at the distal tip of the catheter, the nose cone having a central opening coaxial with the guide wire passage creation means through which the guide wire passage creation means passes when it is moved axially.

4. The device of claim 1, wherein the guide wire passage creation means is a rotating burr.

5. The device of claim 1, wherein the guide wire passage creation means is connected to the proximal end of the catheter by a hollow shaft.

6. The device of claim 5, wherein the guide wire passage creation means is a hollow rotating burr.

* * * * *